United States Patent
Vitali et al.

(10) Patent No.: US 8,909,332 B2
(45) Date of Patent: Dec. 9, 2014

(54) METHOD AND DEVICE FOR ESTIMATING MORPHOLOGICAL FEATURES OF HEART BEATS

(75) Inventors: Andrea Lorenzo Vitali, Bergamo (IT); Marco Pessione, Rivarolo Canavese (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 400 days.

(21) Appl. No.: 13/014,551

(22) Filed: Jan. 26, 2011

(65) Prior Publication Data
US 2011/0184297 A1    Jul. 28, 2011

Related U.S. Application Data

(60) Provisional application No. 61/336,865, filed on Jan. 26, 2010.

(51) Int. Cl.
*A61B 5/0402* (2006.01)
*A61B 5/04* (2006.01)
*A61B 5/0456* (2006.01)
*A61B 5/00* (2006.01)

(52) U.S. Cl.
CPC ............. *A61B 5/0456* (2013.01); *A61B 5/7264* (2013.01); *A61B 5/04017* (2013.01); *A61B 5/7207* (2013.01)
USPC ........... 600/521; 600/508; 600/509; 600/515; 600/517; 600/518

(58) Field of Classification Search
USPC .......... 600/508–509, 515–518, 521; 128/920, 128/923
IPC ...... A61B 5/00,5/04, 5/72, 5/0245; A61N 1/37, A61N 1/025; G06F 19/345; G06K 9/00523; G08B 21/0453; H03H 17/0201; Y10S 128/901, Y10S 706/924
See application file for complete search history.

(56) References Cited

U.S. PATENT DOCUMENTS 4,928,692 A * 5/1990 Goodman et al. ............ 600/324
8,114,021 B2 * 2/2012 Robertson et al. ............ 600/300

OTHER PUBLICATIONS

Hamilton, P. et al., "Quantitative Investigation of QRS Detection Rules Using the MIT/BIH Arrhythmia Database," IEEE Transactions on Biomedical Engineering 33(12):1157-1165, Dec. 1986.
Hamilton, P., "Open Source ECG Anaysis," Computers in Cardiology, vol. 29:101-104, 2002.
Hamilton, P. "Open Source ECG Analysis Software Documentation," E.P. Limited, 2002, 36 pages.
Kohler, B.-U. et al, "The Principles of Software QRS Detection—Reviewing and Comparing Algorithms for Detecting this Important ECG Waveform," IEEE Engineering in Medicine and Biology, pp. 42-57, Jan./Feb. 2002.
Pan, J. et al., "A Real-Time QRS Detection Algorithm," IEEE Transactions on Biomedical Engineering 32(3):230-236, Mar. 1985, & updates.

(Continued)

*Primary Examiner* — Deborah Malamud
(74) *Attorney, Agent, or Firm* — Seed IP Law Group PLLC

(57) ABSTRACT

A method estimates morphological features of heart beats from an ECG signal. Peaks of the R wave of the ECG are detected and classified using a parallel filtering structure. The first branch implements a bandpass filtering with cut off frequencies of about 10 Hz and 35 Hz, enhancing the signal-to-noise ratio (SNR) of the QRS complex. The second branch estimates morphological features of the heart beat from an alternating current (AC) replica of the ECG signal, that may be used to classify the beat and potentially detect arrhythmias.

12 Claims, 10 Drawing Sheets

(56) References Cited

OTHER PUBLICATIONS

Pessione, Marco, "Low-Complexity Adaptive Reliable Electrocardiogram Feature Extraction," Technical University of Turin, Italy, Thesis in Digital Signal Processing, Jan. 14, 2009.

Vitali, A. et al., Collection, Processing and Transmitting Radio Signals to Electronic Biological Patch "BodyGateWay," 9th National Congress of Congress Medical Informatics and Telemedicine, pp. 1-6, Dec. 14-16, 2008, & English Translation downloaded from http://www.efytimes.com/e1/creativenews.asp?edid=63194.

\* cited by examiner

METHOD AND DEVICE FOR ESTIMATING MORPHOLOGICAL FEATURES OF HEART BEATS

BACKGROUND

1. Technical Field

This disclosure relates to signal processing and more particularly to a method of processing an electrocardiogram signal, implemented in a dedicated device or in a microprocessor executing a software code.

2. Description of the Related Art

Electrocardiogram (ECG) signals have a peculiar morphology composed of segments, waves and complexes, as shown by way of example in FIG. 1. A single waveform starts and ends at the baseline, and two consecutive waveforms make a complex. Segments are straight isoelectric lines. Intervals are combinations of waveforms and segments. The baseline is the reference for the slope of the deflection: if the deflection is above the baseline then it is a positive deflection, otherwise it is a negative one.

The P Wave

When the action potential propagates from the sinoatrial (SA) node towards the atrioventricular (A)V node, the atria contract and a de-excitation takes place. This generates the P wave, which normally has a relatively low amplitude (100 µV) and lasts for about 100 ms. The P wave is small rounded, upright and its shape and duration may indicate an atrial enlargement.

The PR Interval

The PR interval is measured between the offset (end) of the P wave and the deflection marking the onset (start) of the QRS complex that represents the conduction of the blood through the atria to the ventricles. It lasts usually from 120 to 200 ms. An interval longer than 200 ms may indicate a first degree heart block.

The QRS Complex

QRS complexes mark the "de-excitation" of the ventricles, resulting in a wave larger than the P wave because of the larger volume of muscular tissue involved. QRS complexes usually have a "width" corresponding to a time interval of 60-100 ms, and if either side of the heart is not functioning properly this "width" may increase. Not every complex contains distinct Q, R and S waves, but any combination of these three waves is conventionally considered a QRS complex. Its importance lies in its magnitude, which is greater than that of any waveform of the ECG signal, making it ideal for a detection algorithm.

The ST Segment

The ST segment is the part of the isoelectric line included between the offset of the QRS complex and the onset of the T wave, representing the time interval between the ventricular de-excitation and its re-excitation. It usually lasts 100 ms. Distinguishing the ST segment from the T wave is often difficult, thus the ST interval is usually considered in its entirety.

The T Wave

Because the ventricular re-excitation is slower than its de-excitation, the T wave is normally wider than the QRS complex, about 200 ms, and usually has a positive deflection. Unfortunately it has a low amplitude, making sometimes difficult its detection. The shape of the T wave is very significant, as it may reveal possible coronary ischemia, hyperkalemia or acute myocardial infarction.

The QT Interval

The QT interval is measured from the onset of the Q wave to the offset of the T wave and it represents the duration of the cycle of de-excitation and re-excitation (i.e., the complete ventricular activity). It normally lasts from 300 to 450 ms, and should be about 40 percent of the interval between two R peaks (R-to-R interval).

Feature Normal Value Limit Associated Pathology

| Feature | Normal Value | Limit | Associated Pathology |
|---|---|---|---|
| P width | 110 ms | ±20 ms | Atrial enlargement |
| PR interval | 160 ms | ±40 ms | Heart block, pericarditis |
| QRS width | 100 ms | ±20 ms | Myocardial infarction |
| αQT interval | 400 ms | ±40 ms | Long & short QT syndrome |
| ST segment | 100 | ±20 ms | Myocardial infarction |
| T width | 200 | ±20 ms | Coronary ischemia, hyperkalemia |
| P amplitude | 0.15 mV | ±0.5 mV | — |
| QRS height | 1.5 mV | ±0.5 mV | — |
| ST level | 0 mV | ±0.1 mV | — |
| T amplitude | 0.3 mV | ±0.02 mV | — |

The above table shows the typical Lead II ECG features and their values for a normal sinus rhythm at a heart rate of 60 bpm in a healthy male adult. The α value for the QT interval varies with the R-to-R interval value and may be computed as $\alpha=(RR)^{0.5}$.

In a real-time monitoring environment where an automated analysis of the heart rate of a patient is performed, every possible noise source affecting the measure must be taken into account. Data corrupted with noise must either be corrected or discarded, as neither unreliable measures nor false warnings are acceptable.

There are several common noise sources affecting an ECG signal. Some of them are related to the acquisition circuit, others are power supply-dependant, finally some are caused by the patient himself:

power-line interference;
electrode loss contact noise;
motion artifacts;
muscle contractions or EMG noise;
baseline drift and amplitude modulation due to patient respiration.

The QRS complex is by far the most important and distinctive feature for the purpose of heart rate measurement. By estimating the time interval between one R wave peak and the next one, it is easy to compute the value of the heart rate, usually indicated in terms of beat-per-minutes. The importance of the QRS complex analysis does not restrict to arrhythmia detection. The duration, amplitude and morphology of this complex is very useful also for the diagnosis of other pathologies, like conduction abnormalities, ventricular hypertrophy, myocardial infarction, electrolyte derangements and other disease states.

Most of known algorithms for QRS detection are based on feature signals obtained using first and second order derivatives of the original signals. They are characterized by a very low computational complexity but, without the aid of empiric rules to reduce the number of false detections, they tend to be very unsatisfactory in presence of noise.

Recent papers have suggested the use of more sophisticated digital alters to enhance the feature signals in the presence of noise events, and they showed much better results than the earlier ones. Lately, many modern signal processing techniques have been applied to QRS detection, and their much heavier computational complexity has resulted in a significant improvement in the algorithm's efficiency, for example through linear and non-linear altering, wavelet transforms, artificial neural networks, genetic algorithms and linear prediction.

Energy thresholding is probably the most well-known and utilized technique for QRS detection. In 1985 Jiapu Pan and Willis J. Tompkins [2] developed an algorithm for the detection of the heart rate in various environments (Holter recordings, ambulatory patients, intensive care units) to discover the presence of dangerous arrhythmias. In 1986 Pat Hamilton and Willis J. Tompkins [3] investigated the quantitative effects of a number of common elements of QRS detection rules implemented in the previous article, improving the performance of the algorithm.

All of these topics are discussed in a review article by Köhler [1].

Unfortunately, the complexity of the prior algorithms is beyond the computational limits of typical micro-controllers of low cost portable devices. Moreover, prior algorithms often make no distinction between noise peaks and R wave peaks, especially with ECG signals corrupted by noise due to motion artifacts or electrode loss contact.

The known algorithms perform poorly in presence of electromyogram (EMG) noise or in the case of electrode loss contact, scoring a noticeable amount of false alarms about patient's conditions.

BRIEF SUMMARY

A novel method of estimating morphological features of heart beats from an ECG signal has been found.

According to one embodiment, peaks of the R wave of the ECG are detected and classified using a parallel filtering structure. The first branch implements a bandpass filtering with cut off frequencies of about 10 Hz and 35 Hz, enhancing the signal-to-noise ratio (SNR) of the QRS complex. The second branch estimates morphological features of the heart beat from an alternating current (AC) replica of the ECG signal, that may be used to classify the beat and potentially detect arrhythmias.

The method may be conveniently implemented in digital form and may be implemented by a hardware device or by a digital signal processor (DSP) or microprocessor unit executing a software code. Some embodiments of the device are capable of working at four different sampling frequencies (128, 256, 512 and 1024 Hz), depending on the accuracy requested.

DETAILED DESCRIPTION

One embodiment avoids possible false alarms about the conditions of a patient monitored with an ECG device, because of noise corrupting the ECG signal.

Figure 1:
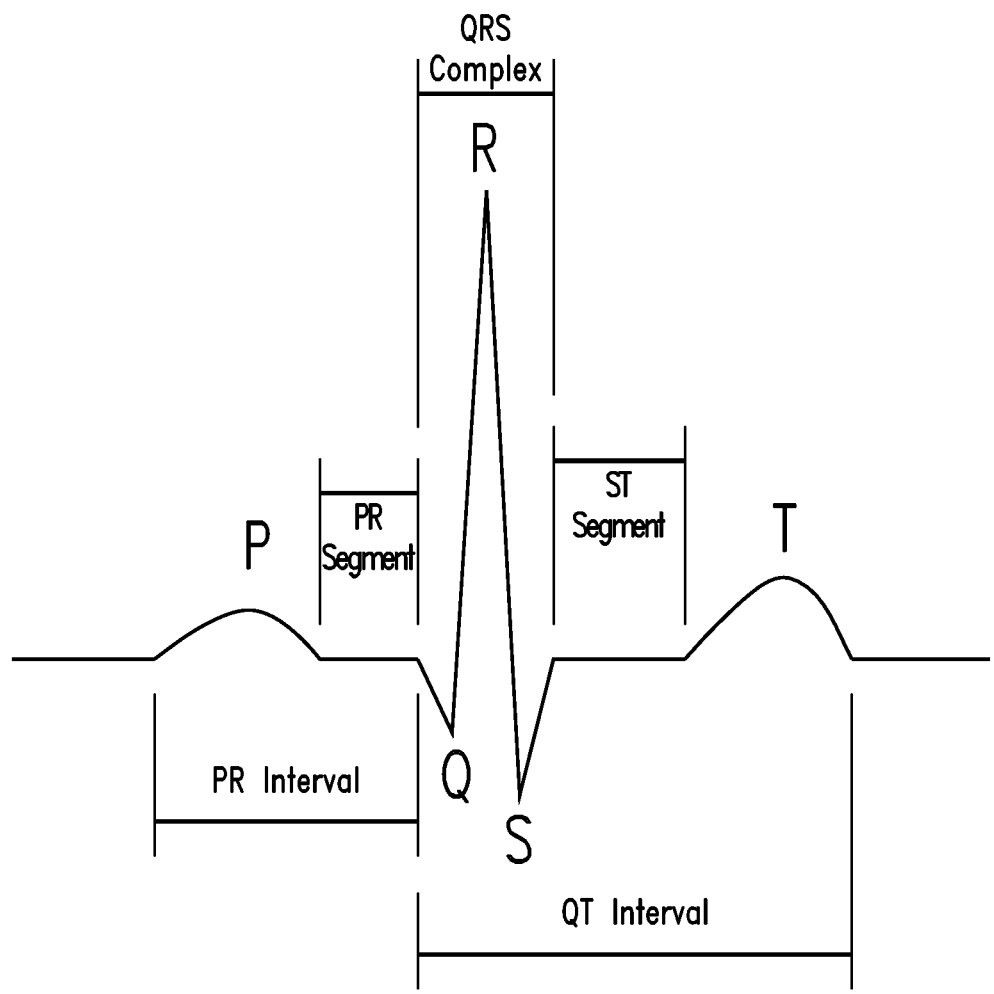
FIG. 1 depicts a typical waveform of an ECG signal.
Figure 2:
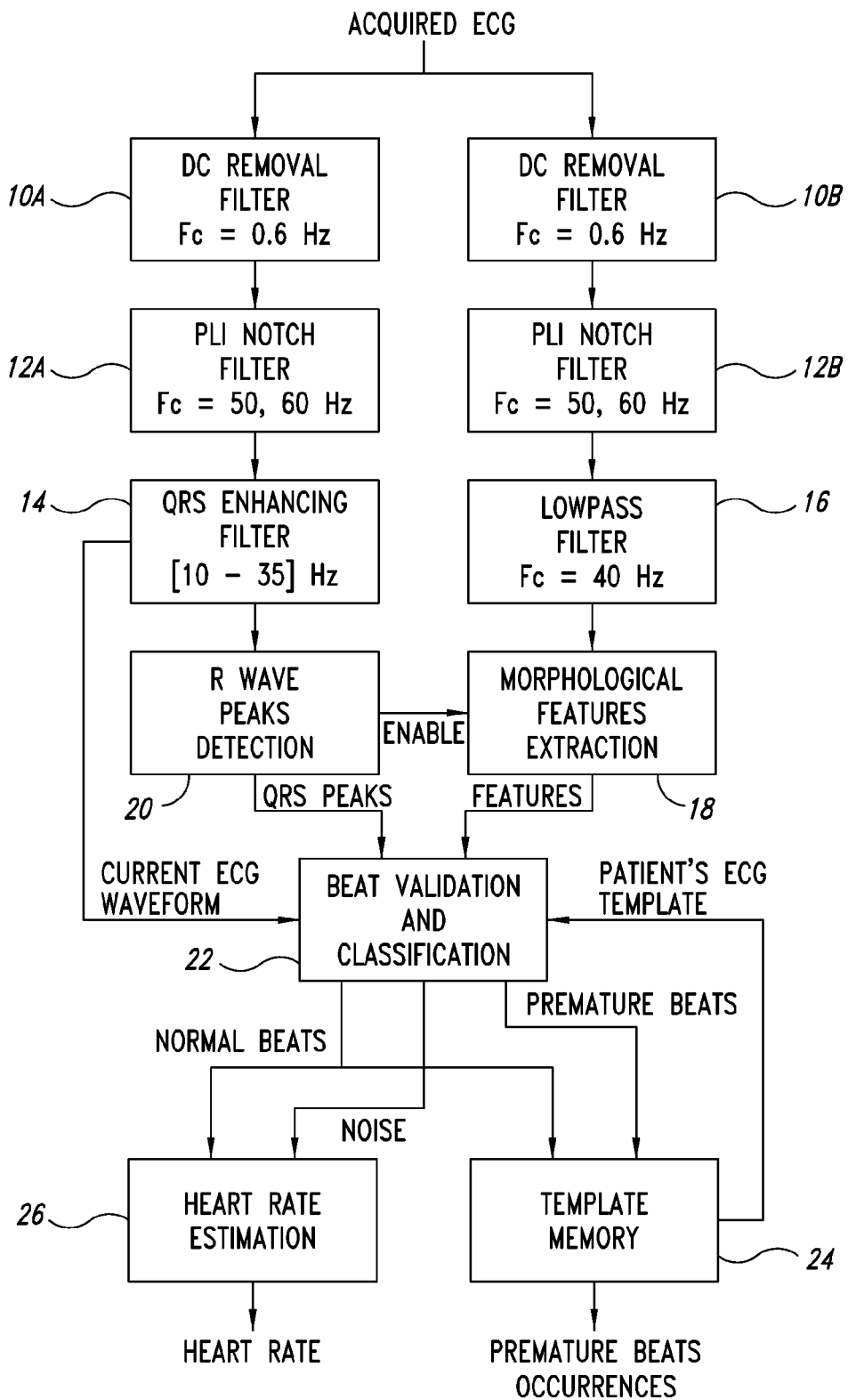
FIG. 2 is a block diagram of a ECG signal processor according to one embodiment, which is configured to implement a novel ECG signal processing method according to one embodiment.

FIG. 2 is a block diagram of a ECG signal processor according to one embodiment, which is configured to implement a novel ECG signal processing method according to one embodiment. The processor can be implemented using one or more of a digital signal processor (DSP), a firmware-controlled microcontroller, and a software-controlled microprocessor.

The process flow may be roughly divided into five different phases:

parallel branch pre-processing;
R wave peaks detection;
estimation of morphological parameters;
validation of the detected beats;
computation of the heart rate.

In one embodiment, the first three steps are implemented for example using the Open Source ECG Analysis (OSEA) software [4].

Parallel Branch Pre-Processing

According to one embodiment shown in FIG. 2, the pre-processing phase can be divided into two different processing branches and has two different purposes: enhance the signal-to-noise ratio of the QRS complex, in order to obtain a feature signal where R wave peaks may easily be distinguished from the peaks belonging to the other waves of the signal (branch #1), and estimate morphological features of the heart beat which will be used for the beat classification (branch #2).

The first two steps of each processing branch are in common.

A direct current (DC) removal filter 10A, 10B processes the acquired ECG signal and is configured to remove the DC component and attenuate baseline wanders typical of motion artifacts and patient movements.

Preferably but not necessarily, a notch filter 12A, 12B is used in order to remove the interference caused by the power-line interference. It has a notch at 50 and 60 Hz, so it is capable of attenuating the power-line interference in both USA and Europe.

In branch #1 a bandpass filter 14 is used to filter out-of-band noise and enhance the energy of the QRS complex.

In the Hamilton-Tompkins algorithm [3], a bandpass filtering is practically carried out on the original ECG signal with a cascade of a low-pass filter and a high-pass filter, resulting in a bandpass filtering between 5 and 12 Hz. This approach has been found inadequate because the energy of the P and T waves extends up to 10 Hz, while the QRS complex has a significant energy between 10 and 35 Hz.

According to an embodiment, found to produce an outstanding enhancement of the detectability of the heart beat period, the bandpass filtering is carried out with a finite impulse response (FIR) bandpass filter 14 between about 10 and about 35 Hz. The filter preferably but not necessarily uses fixed-point coefficients and it has a linear phase response in the band of interest. The length of the filter depends on the used sampling frequency.

This filter has been found to produce far better results than the cascade filters contemplated in the Hamilton-Tompkins algorithm because:
- it uses a lower number of coefficients, resulting in a shorter delay;
- it damps more effectively the P and T waves;
- it enhances more significantly the QRS complex.

Moreover, in one embodiment, the novel processing algorithm is designed to work at four different sampling frequencies, while the Hamilton-Tompkins algorithm is specifically designed to work only at 200 Hz.

Figure 3:
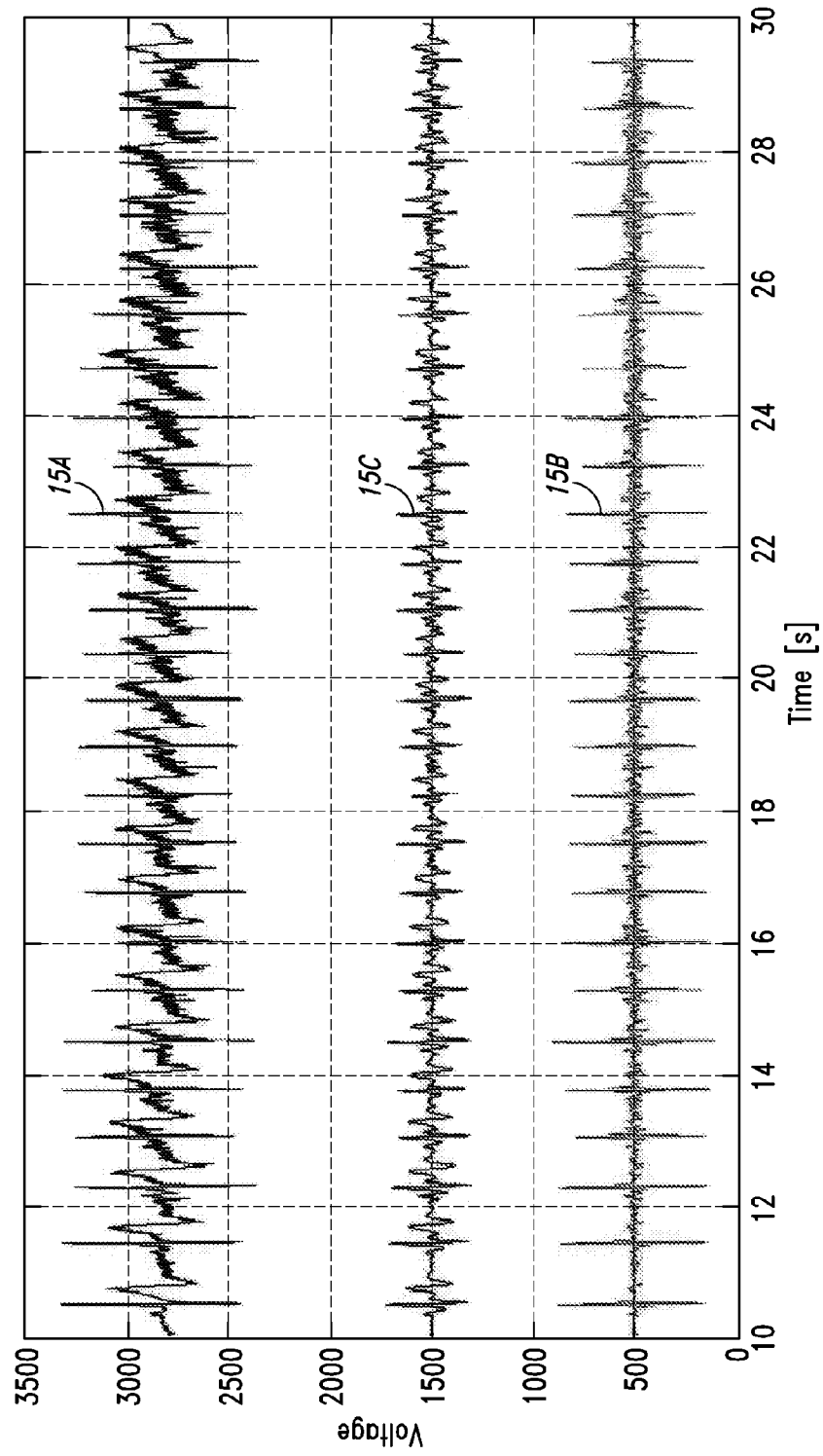
FIG. 3 compares a poor quality ECG signal with two filtered replica thereof obtained with the proposed band-pass filter and with the filtering carried out by the Open Source ECG Analysis (OSEA) software.
Figure 4:
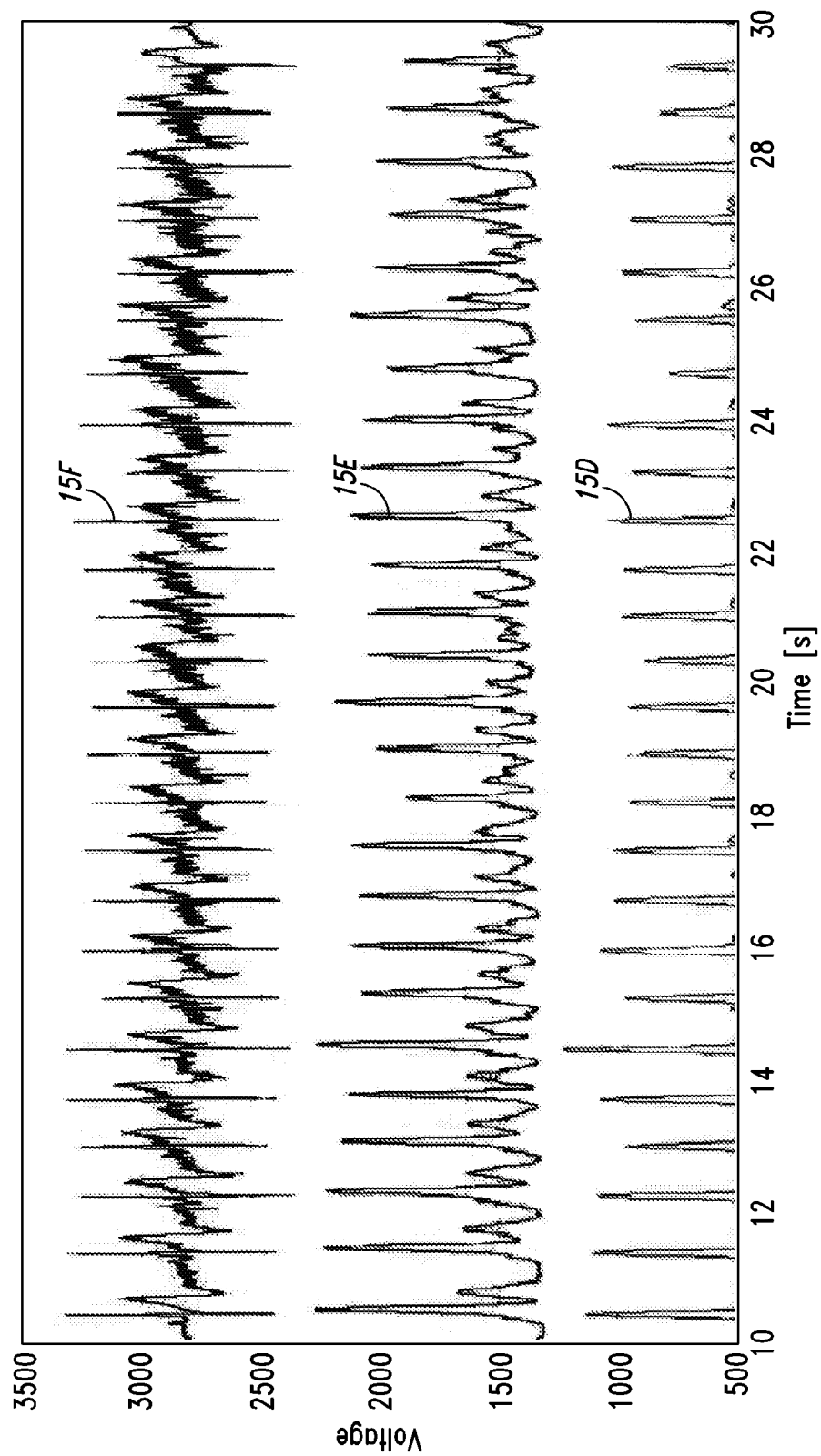
FIG. 4 compares a poor quality ECG signal with two filtered replica thereof obtained with a DC filtering followed by the Hamilton-Tompkins algorithm, and with the OSEA Enhancing Feature filtering, respectively.

The drawback of the novel processing is the attendant introduction of a distortion that alters the points of the Q and S peaks. FIG. 3 compares simulation results comparing an original ECG signal 15A strongly corrupted by noise, a bandpass-filter signal 15B obtained by bandpassing the ECG signal 15A with the bandpass filter 14, and a filtered signal 15C according to the Hamilton-Tompkins algorithm. FIG. 4 compares simulation results comparing the original ECG signal 15A, a filtered signal 15D obtained by filtering the ECG signal 15A with both the DC filter 10A and the bandpass filter 14, and an enhanced filtered signal 15E according to the Hamilton-Tompkins algorithm.

According to the embodiment shown in FIG. 2, the ECG signal is processed also with a second branch. After the DC-removal and PLI filtering, a lowpass filter 16 is used in order to filter out high frequency components typical of noise without introducing any distortion on the ECG signal.

The DC filter 10A, 10B may be implemented very efficiently with a certain number of additions and a bit-shift.

It will of course be recognized that the DC filters 10A, 10B could be implemented as a single DC filter and the notch filters 12A, 12B could be implemented as a single notch filter such that the passband filter 14 and the lowpass filter 16 both operate on the same signal output by the single notch filter, or entirely independent filter branches could be employed as illustrated in FIG. 2.

From this point onwards, the signal filtered in branch #2 may be processed by a feature extractor 18 for extracting morphological features of the heart beat. The point of the R wave is detected using the slope of the lowpass filtered signal, and, using that point as a reference, several important morphological features of the heart beat (QRS complex width, R wave peak height, R wave peak sign, PR interval length) are estimated. This operation is performed in response to receiving an enable signal from an R wave peak detector 20, which produces the enable signal upon detecting a QRS complex.

R Wave Peak Detection

Detection of peaks of the R wave by the R wave peak detector 20 is obtained by processing the bandpass filtered replica of the ECG signal as in the Hamilton-Tompkins algorithm [3]. The bandpass filtered signal is non-linearly enhanced using a slope filter and a moving average filter, resulting in a bump-like feature signal where the highest peaks mark the occurrences of the QRS complex. Every peak above a threshold determined in an adaptive fashion is marked as belonging to the useful signal, and every peak below the threshold is recognized as a noise peak. The current estimates of the signal peaks and the noise peaks are processed as usual in the Hamilton-Tompkins algorithm for updating the threshold.

Some parameters however were changed, because the distortion introduced by the QRS-enhancing filter 14 produced a feature signal characterized by a higher number of ripples. For this reason, the conditions used for the identification of the peak were constrained:
- the signal returns to a 1/16 of the highest peak value;
- 95 ms have passed since the highest peak index.

These changes are advisable in order to correctly identify a peak both in the presence of noise and during premature events (premature atrial contractions (PACs), premature ventricular contractions (PVCs), tachycardias, etc.).

Estimation of Morphological Features

Whenever a R wave peak is detected, the lowpass filtered signal is used by the feature extractor 18 for the estimation of the morphological features. These features will help in determining the nature of the QRS complex identified. They are:
- width of the QRS complex;
- magnitude of the R wave peak of the QRS complex;
- sign of the peak detected.
- length of the PR interval To get a rough estimation of the width of the QRS complex, its onset and the offset are determined.

Several techniques have been presented in literature to accomplish this task. The most straightforward and sensitive is the one disclosed in the documentation of the Open Source ECG Analysis (OSEA) software [5], incorporated herein by reference in its entirety. Starting from the R wave peak, we move right and left until a five-points segment has a range which is within a given range (while using the raw signal) or until a three-points segment is below a certain threshold (while processing the slope signal). If the estimates based on the raw signal are near enough the estimates based on the slope, then they become the final estimates. Otherwise, the slope-based estimates are taken as the true ones. The assessment of the sign and magnitude of the R wave peak is instead much easier, since the R wave peak position is the intrinsic outcome of the QRS detection algorithm. The magnitude is the value of the highest peak detected with the peak detection algorithm, the sign is positive whenever this value is greater than 0 and negative otherwise.

The R wave peak detector 20 uses an improved version of the OSEA approach in one embodiment. First, the R wave peak is more accurately detected as the zero crossing between the two absolute maxima in the slope of the lowpass filtered signal, choosing the R wave peak as the sharpest peak in the waveform. Then the QRS complex width is computed as a mean between the width estimated using the lowpass signal and the width estimated using the slope signal. This helps in obtaining a more robust estimate, especially in the case of weird ECG morphologies.

Another important morphological feature that is really useful in the detection of premature beats is the morphology of the P wave. As a matter of fact, its shape is important in distinguishing a normal beat from a premature atrial contraction. The P wave is detected as the highest peak in a 200 ms time window preceding the R wave peak, starting 250 ms and ending 50 before the R wave peak.

Validation of the Detected Beats

A beat validation module 22 of the ECG analysis processor of FIG. 2 has three main functions:
- improve the detection of normal beats performed by the Hamilton-Tompkins modified version of the algorithm;
- obtain an estimation of the typical waveform of the ECG of the patient;
- record the occurrence of eventual premature contractions and the specific waveform of each type of them.

The Hamilton-Tompkins algorithm doesn't provide an adequate noise rejection in case of EMG interference or during the events of electrode loss contact. The task of the beat validation module 22 is to handle these events and minimize the number of false alarms detected.

The first step in this processing is the identification and storage of the typical waveform of the patient. Every person has a specific waveform, which is the result of the electrical activity of the heart during a normal heartbeat. Therefore the typical electrocardiogram of a healthy subject may be considered as a simple sequence of identical waveforms. The estimation of the heart rate in this case is very simple, as it includes identifying the consecutive peaks and measuring the time interval occurring between them. Whenever this sequence of equal waves is disrupted, it means that something has happened during our recording. These events are the outcome of two possible facts:

nothing changed in the heart of the patient, but a noise source is affecting the signal, potentially leading to a wrong estimation;

the heart of the patient is experiencing an arrhythmia or a unexpected condition.

The beat validation module 22 is configured to discriminate between these events. There are several methods that may be used to detect the occurrence of these events, such as, for example, the estimation of correlation and variance.

Variance

Many noise sources affecting electrocardiogram signals are characterized by steep slopes and high-amplitude swings, noticeably larger than the slopes and the swings of the typical PQRST waveform. If we compare the variance of the patient's template with the variance of the portion of the signal under analysis, we may obtain an estimation of the similarity between the two data sequences. There are numerous algorithms for the estimation of the variance:

Naïve algorithm;
Two-pass normal algorithm;
Two-pass compensated variant;
Knuth's online algorithm.

Whilst Knuth's online algorithm may be considered the best algorithm because of its intrinsic speed, since it is a single pass algorithm, the compensated variant of the two-pass algorithm seems to be more advisable because it does not request more than two divisions. Both algorithms may be efficiently performed with simple bit-shifts, while analyzing data segments with a power-of-2 length.

A C-like pseudo-code that illustrates the compensated variant of the two-pass algorithm is:

```
n = sum1 = 0;
for i = 1 to N do
    x = data[i];
    n = n + 1;
    sum1 = sum1 + x;
end for
mean = sum1 / n;
sum2 = 0;
sumc = 0;
for i = 1 to N do
    x = data[i];
    sum2 = sum2 + (x − mean)2;
    sumc = sumc + (x − mean);
end for
var = (sum2 − (sumc2 / n)) / (n − 1);
```

In order to get an estimate numerically similar to the correlation, we compute a variance coefficient:

$$VC = \left| \frac{VAR_X - VAR_{REF}}{VAR_X + VAR_{REF}} \right| \quad (1)$$

where the deponent REF indicates the data sequence corresponding to the typical patient's waveform and the deponent X indicates the portion of the data under analysis. This coefficient is very close to 0 when the two data sequences have similar variance, while it is near 1 when one of the two variances (in our case, the variance of the portion of data under analysis) is relevantly larger than the other.

Template Memory

The ECG analysis system of FIG. 2 includes a template memory 24 that stores a typical template of the electrocardiogram corresponding to the heartbeat of the patient for use as a reference for comparison. This allows the ECG analysis system of FIG. 2 to identify the occurrences of events in which the electrocardiogram is clearly different from the normal waveform of the patient The template memory may contain all important information about the analysis of the electrocardiogram. This memory may be ideally organized into the following fields:

a waveform field, consisting in a N-by-L beat matrix which contains the waveform of the N most recurrent beat templates (each waveform is stored as a vector L samples long);

a var field, where the variances of the N templates are stored;

a sign field, where the sign of the R wave peak of each template is stored;

a height field, where the magnitudes of the R wave peaks are memorized;

a qrswidth field, containing the width of the QRS complex for each template;

a count field, where is recorded the number of occurrences of each of the templates so far;

a pos field, consisting in a N-by-M matrix which contains the positions in the data stream of the occurrences of the various templates;

a use field, an integer value indicating which is the most recurrent ("dominant") template among the ones stored in the beats field.

The choice of N (number of templates to be stored) and M (number of previous beat indexes to memorize) is based on the computational power available and on the speed of the processor. As a matter of fact, the number of template stored increases the time required for the correlation and variance checks. A significant part of the template memory 24 is devoted to the memorization of the template of the premature ventricular contractions (PVCs) detected. Obviously the PVC Memory contains the same fields as the template memory.

Algorithm Logic

The beat validation module 22 employs a start-up phase. In this processing step the algorithm performs a preliminary estimation of the R-to-R interval, which will be used later to detect the premature beats, and to store the template of the patient's specific waveform into the template memory 24. According to an embodiment of the novel algorithm, the start-up phase lasts for eight beats.

In this initial stage, the template memory 24 is initialized with the template of a typical QRS complex. This complex is used as a reference for the computation of the correlation and variance coefficients, and as soon as a heartbeat with high correlation and low variance is detected, this starting template is overwritten with the waveform of the beat acknowledged.

From now on whenever the patient's specific template is used to perform the correlation and variance check, and the results from these computations are satisfying, the template in memory is updated with the average between the past template and the new waveform.

Thanks to this process, the algorithm is actually capable of adapting to the time-varying nature of the electrocardiogram of the patient. As soon as enough beats are validated, the average R-to-R interval is computed as the geometric mean of the R-to-R interval recorded so far. Several checks are performed before the computation of correlation and variance, and their main goal is to detect the occurrences of PACs and PVCs:

Prematurity: if the R-to-R interval between the previous normal beat and the current peak is shorter than the 75% of the current R-to-R interval average, the current beat is marked as "premature".

Amplitude: if the amplitude of the current peak is above 150% or below 50% the amplitude of the R wave peak of the current dominant template, the beat is very likely to be a PVC.

Width: if the width of the QRS complex of the current peak is 150% larger or 50% shorter than the width of the QRS complex of the current dominant template, the beat is very likely to be a PVC.

Sign: if the sign of the current peak is different from the sign of the R wave peak of the current dominant template, there are good chances that the current beat is a PVC.

Correlation: if the correlation between the current beat and the dominant template is between 0.5 and 0.85, the beat is probably a PVC.

Combining the results of this checks with the ones of the correlation and variance check, we may characterize the detected beat and perform a preliminary classification. Table 1 summarizes the rules used for the classification.

TABLE 1

| Beat Type | Prem. | Ampl. | Width | Sign | Correlation | Variance |
|---|---|---|---|---|---|---|
| Normal | x | x | x | x | >0.85 | <0.25 |
| PAC | ✓ | x | x | x | >0.85 | <0.25 |
| PVC #1 | ✓ | ✓ | ✓ | ✓ | 0.5-0.9 | 0.25-0.7 |
| PVC #2 | — | ✓ | ✓ | x | 0.5-0.9 | 0.25-0.7 |
| Noise | — | — | — | — | <0.5 | >0.7 |

Note that since a premature atrial contraction has almost the same morphology of a normal beat (the P wave may be slightly different, but detecting this change is a challenging task), its classification relies only its prematurity. On the other hand, the two possible types of premature ventricular contraction present similar characteristics (different morphology, a higher variance and a broader QRS complex), but since their peaks have different sign, they are divided into two different classes for the classification.

Whenever a PVC is detected its waveform is stored in the reserved block of the template memory 24, and each occurrence of each PVC type is stored. As soon as some premature ventricular contractions are detected, their waveforms are used to improve the PVC detection by comparing the candidate PVC with the templates memorized.

By counting the consecutive occurrences of PACs and PVCs, the algorithm is capable of detecting two different types of arrhythmia. Whenever three or more consecutive PVCs are detected, a ventricular tachycardia is detected. If instead we have three or more consecutive PACs, a supraventricular tachycardia (SVT) is detected.

Estimation of the Heart Rate

Every time a normal beat is detected, the current R-to-R interval is estimated and it is used by a heart rate estimator 26 to compute the current heart rate. If the preceding beat is a PVC or a PAC, the estimate is not performed because during arrhythmias such as ventricular or supraventricular tachycardia the resulting heart rate would be much greater than the real one. For this reason, only normal beats are employed for the calculation of the heart rate.

The duration in seconds of the R-to-R interval at time index n may be computed as:

$$RR_n = \frac{BeatIndex_n - BeatIndex_{n-1}}{fs} \quad (2)$$

Before calculating the corresponding heart rate, an average of the last N R-to-R intervals is computed. This operation has the purpose of attenuating eventual wrong detections, and the choice of the number of beats used for the average is a very sensitive issue. This value should be chosen carefully because, if it is too high, the resulting estimate will not be able to adapt fast enough to an accelerating heart rate. On the other hand, if a too low value is used, the estimate will be affected by possibly wrong detections.

The suggested number of beats is N=10, but we instead chose N=8 as it is the closest power-of-2 available:

$$RR_{MEAN} = \frac{RR_n + \ldots + RR_{n-N+1}}{N} \quad (3)$$

The corresponding heart rate, measured in beat-per-minutes, is calculated with the formula:

$$HR_n = \frac{60}{RR_{MEAN}} \quad (4)$$

The output of our algorithm is updated only when a new normal beat is detected.

Otherwise, the output simply holds to the last computed heart rate. However if many noise beats are detected or no normal beat is detected for a given time, an alert may be issued to the user because something is clearly wrong with the acquisition of the signal.

We present a complete system for the processing of the electrocardiogram (ECG) signal. The purpose of the system is the estimation of the heart rate, a vital parameter which is crucial in assessing the heart condition.

The system comprises a double filtering chain, which is responsible for the heart beat detection and classification, leading to a reliable estimate of the heart rate.

The system may be improved with the addition of two branches which detect possible noise sources affecting the ECG signal, and may be even enhanced with additional branches designed for the estimation of the heart rate from different biological sources (e.g., photoplethysmography, bio-impedance, phonocardiogram, etc.).

When dealing with wearable devices, several key-factors should be taken into account.

The computational power of the micro-controller is limited, therefore every processing step should be performed using as few resources as possible. That's why every filter uses only fixed-points coefficients and almost every operation is performed with sums and bit-shifts, keeping the number of multiplications and divisions at minimum. This approach will help the battery of the device in lasting longer, improving the duration of the analysis and less frequently requiring a recharge.

Another key feature of the embodiment shown in FIG. 2 is the capability of delivering a real-time estimation. Detection and characterization of premature beats are important to achieve a reliable estimation of the heart rate. Many rhythm-related pathologies cause the occurrence of a remarkable number of premature beats, which should be discarded in the computation of the heart rate. Moreover the identification of the different waveforms of the premature ventricular contractions is particularly interesting in patients needing pacemaker implantation. By understanding where the most recurrent ectopic beat originates in the heart, the cardiologist may gain a more thorough knowledge of the patient physiology and eventually perform a more effective surgery.

Finally, the embodiment of FIG. 2 is able to adapt to the specific patient heartbeat waveform. It is independent of the electrode placement and is able to adapt to the evolution of the patient's electrocardiogram over time.

The embodiment may run on wearable devices with the purpose of continuous health monitoring. These systems usually incorporate a micro-controller (sometimes even a microprocessor) and sensors designed to acquire several physiological sources from the patient.

Figure 5:
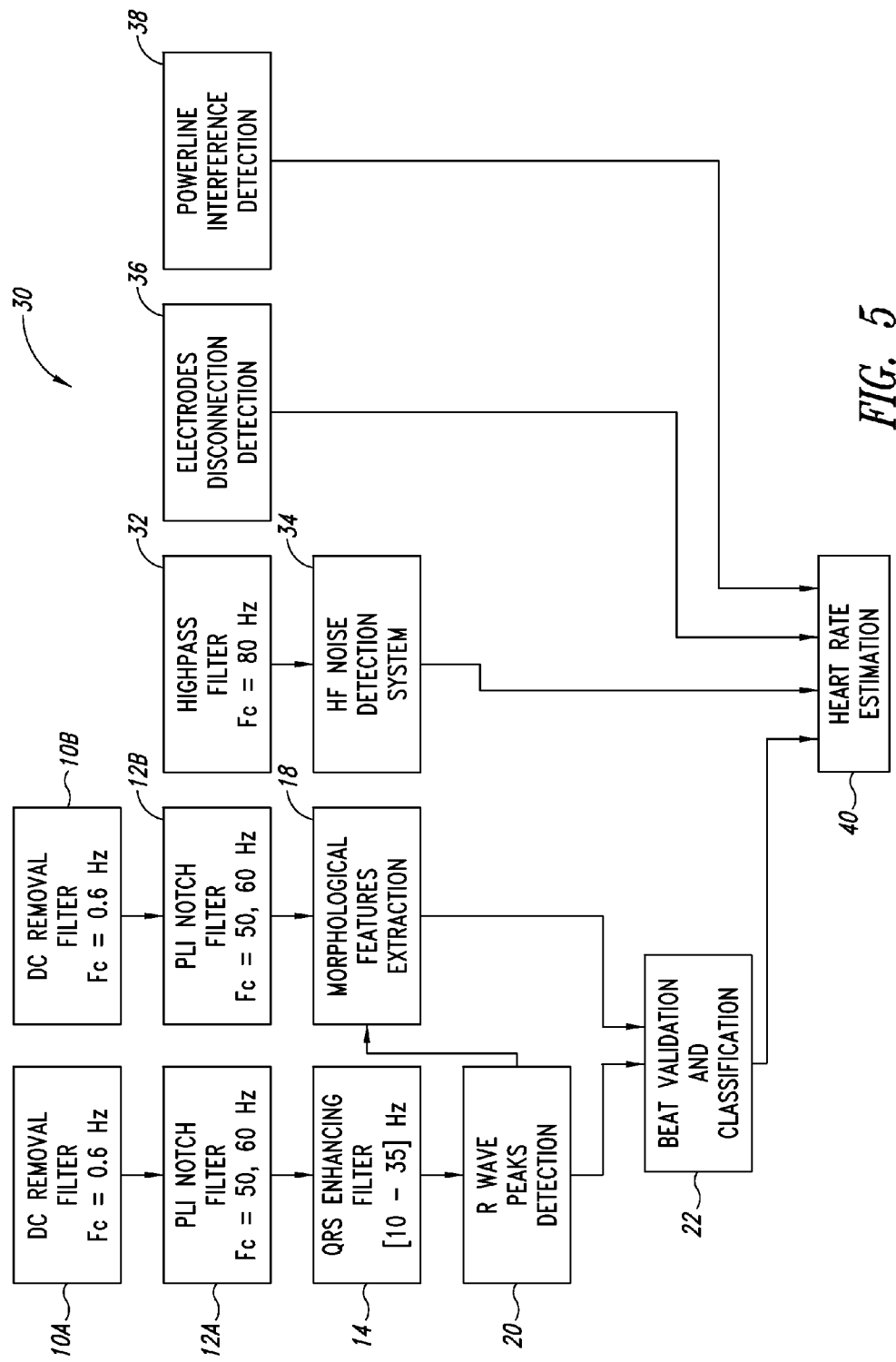
FIG. 5 is a flow chart that illustrates another embodiment of the novel method.

The block diagram of FIG. 5 of another embodiment of a processor 30 is divided into branches. The first branch is responsible for detecting the occurrence of a heart beat. It employs the digital filters 10A, 12A, and 14 and the R wave peak detector 20 in order to generate an AC signal for extracting morphological features and a bandpass filtered signal where the presence of a QRS complex is detected using an improved version of the Hamilton-Tompkins algorithm [3]. This branch performs a strict bandpass filtering with the goal of enhancing the energy of the QRS complex in the signal. Unfortunately this procedure causes an alteration of the heartbeat waveform, which is unsuited for any kind of morphological measurement.

Therefore the morphological feature extraction is performed by the feature extractor 18 in the second branch of the system, where the DC filter 10B removes the DC component, the power line interference and the high-frequency noise from the signal, without changing its morphology. The outputs of the first two branches are then received by the beat validation and classification module 22: the patient specific QRS complex waveform for a normal beat is recognized and used as a reference for the subsequent comparisons. The morphological features are used to classify the beat as normal, PAC (premature atrial contraction) or PVC (premature ventricular contraction), providing a detection of basic arrhythmias as well (ventricular and supraventricular tachycardia).

Like the embodiment illustrated in FIG. 2, the frequency components in the neighborhood of the supply frequency (50 Hz in Europe, 60 Hz in USA) are filtered out from the ECG signal with a PLI (Power Line Interference) notch filter 12B.

Also from the signal to be bandpassed by the QRS enhancing filter 14 the DC component thereof is removed by the DC filter 10A. This operation may appear unnecessary because the DC component is also filtered out by the bandpass filter. Adding this operation does not alter the results and allows to use a same replica of the ECG signal, filtered from the DC component and the frequency components in the neighborhood of the supply frequency, both in the QRS enhancing filter and in the functional block for extracting morphological features of the heartbeat signal.

The third branch includes a high pass filter 32 and a noise detector 34 to detect high frequency noise affecting the signal. This type of noise is usually due to electromyographic interference (muscle activity) and low quality electrode contact. If the high frequency noise is too high, a warning is issued about the reliability of the heart rate estimation.

The fourth branch includes an electrode detector 36 configured to detect any disconnection of the electrodes from the chest of the patient. This branch is capable of detecting both disconnection events and disconnected acquisitions, issuing a similar warning about the unreliability of the estimation.

The fifth branch includes a powerline interference detector 38 configured to detect powerline noise.

The outputs of the branches are then provided to a heart rate estimator 40, leading to an extremely reliable estimation of the heart rate of the patient.

Figure 6:
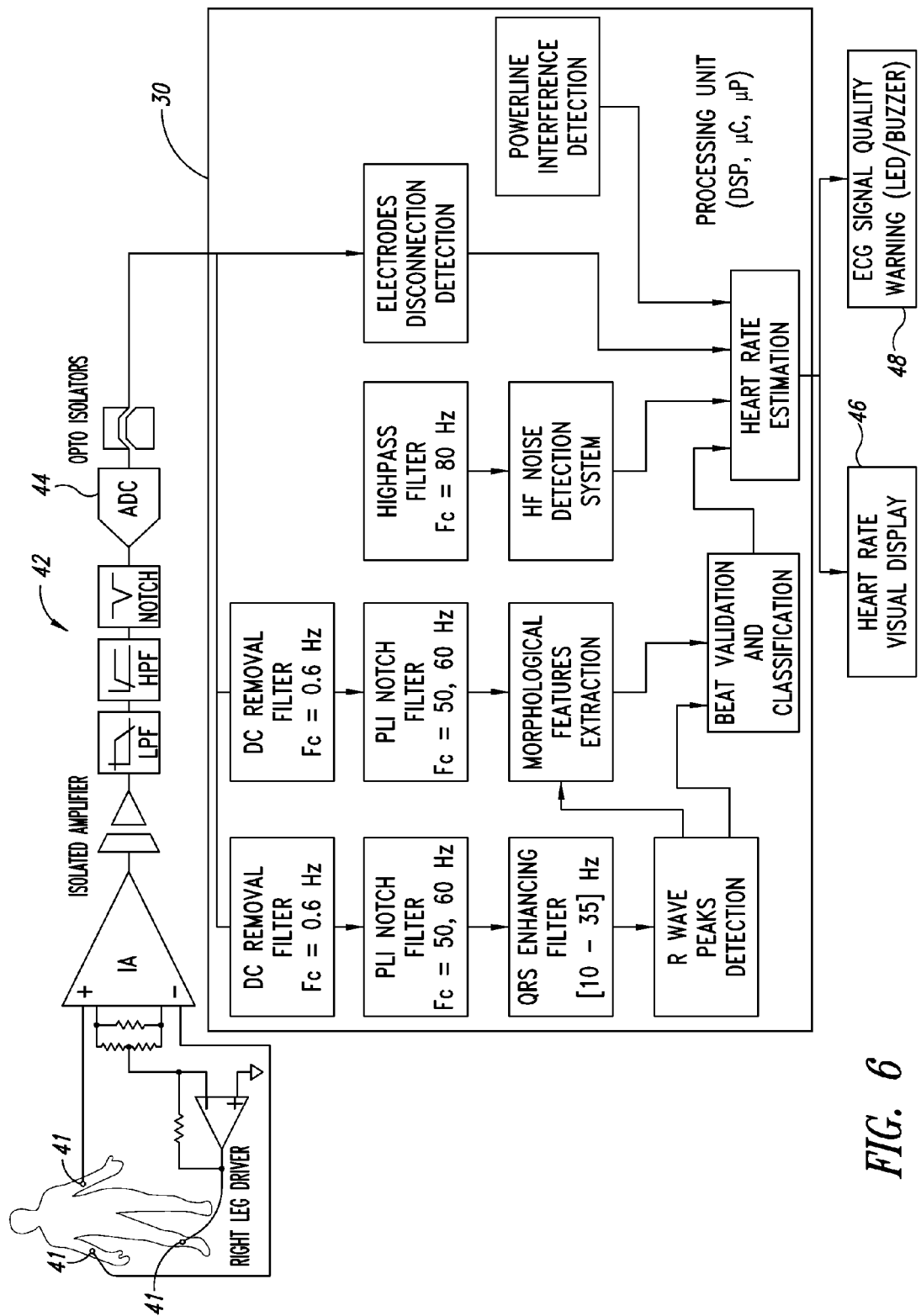
FIG. 6 depicts a hardware heart rate monitoring system including a DSP that implements the method of FIG. 5.

An exemplary embodiment of a novel monitoring system that includes the processor 30 illustrated in FIG. 5 is shown in FIG. 6. The system includes an analog front-end 42 connected to the body of a patient and configured to generate a filter analog signal that is converted into digital form by an analog-to-digital converter (ADC) 44, then supplied to the processing unit 30. The processing unit 30 may be for example a DSP, a microcontroller, a microprocessor etc., or any combination thereof, that performs the novel method.

In the example of FIG. 6, the processing unit implements the method discussed above with respect to FIG. 5, but the same arrangement may be used for implementing any novel method disclosed herein.

The first two branches may be considered the core of the system and they offer reliable estimations. The third and fourth branches may be optionally added to increase the reliability of the algorithm in specific cases (EMG noise, electrode loss contact).

The ECG signal is acquired using a set of electrodes 41 and a typical analog front-end 42 and then processed by the processing unit 30. The reliable heart rate estimation is displayed on a monitor 46. The system also includes a warning indicator 48 configured to provide a visual/audio warning about the reliability of the acquisition.

Branch #1: QRS Detection

The first branch consists of four blocks:

DC Removal Filter

PLI Notch Filter

QRS Enhancing Filter

R Wave Peaks Detection

Figure 7:
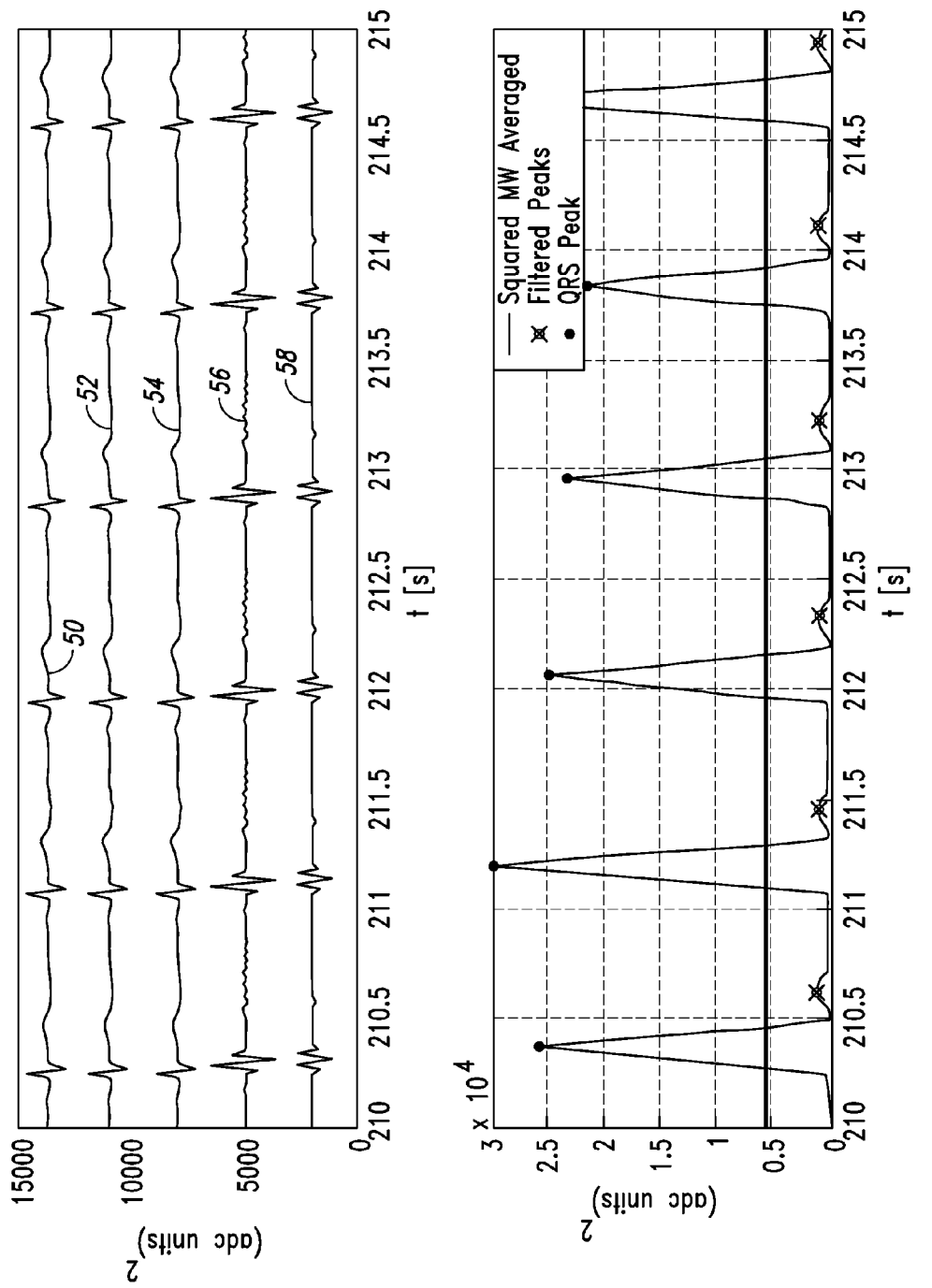
FIG. 7 compares an original ECG signal with the filtered replica thereof generated by the various functional blocks in FIG. 5.

The effect of each step of the processing is exemplified in FIG. 7. The upper image shows a raw ECG signal 50 received by the processing unit 30, a DC filtered signal 52 output by the DC filter 10A, a notch-filtered signal 54 output by the notch filter 12A, a QRS enhanced signal 56 output by the QRS filter 14, and a slope signal 58 produced by the R wave peak detector 20. The lower image of FIG. 7 represents the energy of the QRS complex, where the highest peaks are related to the peaks of the R waves.

DC Removal Filter

This filter 12A is designed to remove the DC component from the ECG signal and attenuate possible baseline wanders due to motion artifacts. These tasks are accomplished with a FIR high-pass filter which subtracts from the current sample the mean value of the previous N samples. It is implemented with the difference equation:

$$y_n = x_n - \frac{1}{N}[x_{n-1} + \ldots + x_{n-N}] \quad (5)$$

The choice of the N parameter depends on the operative sampling frequency and may be determined, for example, according to Table 2.

TABLE 2

DC Removal Filter Length

| Fs [Hz] | DC Filter Length [samples] |
|---|---|
| 128 | 32 |
| 256 | 64 |
| 512 | 128 |
| 1024 | 256 |

PLI Notch Filter

The function of this filter 12A is to remove or at lease damp noise related to the power-line interference. This noise is characterized by a specific frequency component of 50/60 Hz, according to the country, and is filtered using a FIR notch filter, whose length and coefficients change according to the specific sampling frequency, for example, according to Table 3.

TABLE 3

PLI Notch Filter Coefficients

| Fs [Hz] | h(n) | gain |
|---|---|---|
| 128 | $[0, -\frac{1}{8}, 0, \frac{1}{2}, \frac{1}{2}, 0, -\frac{1}{8}, 0]$ | $\frac{1}{4}$ |

TABLE 3-continued

PLI Notch Filter Coefficients

| Fs [Hz] | h(n) | gain |
|---|---|---|
| 256 | $[1, 1, 1, 3, 0, 2]$ | $\frac{1}{4}$ |
| 512 | $[1, 0, 0, 0, 1, 1, 0, 0, 0, 1]$ | $\frac{1}{2}$ |
| 1024 | $[1, 0, 0, 0, 0, 0, 0, 0, 1, 0, 1, 0, 0, 0, 0, 0, 0, 0, 1]$ | $\frac{1}{2}$ |

QRS Enhancing Filter

This block 14 performs a strict bandpass filtering in the range of the QRS complex, enhancing its waveform and attenuating out-of-band noise. Its bandpass is between 10 and 35 Hz and it is implemented with a FIR filter, whose length and coefficients depend on the sampling frequency, for example, according to Table 4.

TABLE 4

QRS Enhancing Filter Coefficients

| Fs [Hz] | h(n) | gain |
|---|---|---|
| 128 | $\left[\frac{1}{64}, -\frac{6}{64}, -\frac{13}{64}, -\frac{7}{64}, \frac{11}{64}, \frac{21}{64}, \frac{11}{64}, -\frac{7}{64}, -\frac{13}{64}, -\frac{6}{64}, \frac{1}{64}\right]$ | 2 |
| 256 | $\left[-\frac{4}{32}, -\frac{3}{32}, -\frac{1}{32}, \frac{3}{32}, \frac{6}{32}, \frac{7}{32}, \frac{6}{32}, \frac{3}{32}, -\frac{1}{32}, -\frac{3}{32}, -\frac{4}{32}\right]$ | 2 |
| 512 | $\left[\begin{array}{l} 0, 0, -\frac{1}{64}, -\frac{2}{64}, -\frac{2}{64}, -\frac{3}{64}, -\frac{3}{64}, -\frac{4}{64}, -\frac{3}{64}, -\frac{3}{64}, -\frac{2}{64}, \\ 0, \frac{1}{64}, \frac{3}{64}, \frac{4}{64}, \frac{5}{64}, \frac{6}{64}, \frac{6}{64}, \frac{6}{64}, \frac{5}{64}, \frac{4}{64}, \frac{3}{64}, \frac{1}{64}, 0, -\frac{2}{64}, \\ -\frac{3}{64}, -\frac{3}{64}, -\frac{4}{64}, -\frac{3}{64}, -\frac{3}{64}, -\frac{2}{64}, -\frac{2}{64}, -\frac{1}{64}, 0, 0 \end{array}\right]$ | 2 |
| 1024 | $\left[\begin{array}{l} -\frac{1}{64}, -\frac{1}{64}, -\frac{1}{64}, -\frac{1}{32}, -\frac{1}{32}, -\frac{1}{32}, -\frac{1}{32}, -\frac{1}{32}, -\frac{1}{32}, -\frac{1}{32}, -\frac{1}{32}, -\frac{1}{64}, \\ -\frac{1}{64}, -\frac{1}{64}, -\frac{1}{64}, 0, 0, 0, \frac{1}{64}, \frac{1}{64}, \frac{1}{64}, \frac{1}{32}, \frac{1}{32}, \frac{1}{32}, \frac{3}{64}, \\ \frac{3}{64}, \frac{3}{64}, \frac{3}{64}, \frac{3}{64}, \frac{3}{64}, \frac{3}{64}, \frac{3}{64}, \frac{3}{64}, \frac{1}{32}, \frac{1}{32}, \frac{1}{32}, \frac{1}{64}, \\ \frac{1}{64}, 0, 0, 0, -\frac{1}{64}, -\frac{1}{64}, -\frac{1}{64}, -\frac{1}{64}, -\frac{1}{32}, -\frac{1}{32}, -\frac{1}{32}, -\frac{1}{32}, \\ -\frac{1}{32}, -\frac{1}{32}, -\frac{1}{32}, -\frac{1}{32}, -\frac{1}{64}, -\frac{1}{64}, -\frac{1}{64} \end{array}\right]$ | 2 |

R Wave Peaks Detection

The bandpass filtered signal is then processed with a slope filter of the R wave peak detector 20, which enhances the steepness of the QRS complex. The coefficients of the slope filter for each specific sampling frequency may be determined, for example, according to Table 5.

TABLE 5

Slope Filter Coefficients

| Fs [Hz] | h(n) | gain |
|---|---|---|
| 128 | $\left[-\frac{1}{2}, 0, \frac{1}{2}\right]$ | 3 |

TABLE 5-continued

Slope Filter Coefficients

| Fs [Hz] | h(n) | gain |
|---|---|---|
| 256 | $\left[-\frac{1}{4}, -\frac{1}{2}, 0, \frac{1}{2}, \frac{1}{4}\right]$ | 2 |
| 512 | [−4, −3, −2, −1, 0, 1, 2, 3, 4] | 1 |
| 1024 | [−8, −7, −6, −5, −4, −3, −2, −1, 0, 1, 2, 3, 4, 5, 6, 7, 8] | 1 |
| 128 | $\left[0, -\frac{1}{8}, 0, \frac{1}{2}, \frac{1}{2}, 0, -\frac{1}{8}, 0\right]$ | 1 |
| 256 | $\left[-\frac{1}{16}, -\frac{1}{16}, 0, \frac{1}{8}, \frac{1}{4}, \frac{5}{16}, \frac{1}{4}, \frac{1}{8}, 0, -\frac{1}{16}, -\frac{1}{16}\right]$ | 1 |
| 512 | $\left[\frac{1}{32}, \frac{1}{16}, \frac{3}{32}, \frac{1}{8}, \frac{5}{32}, \frac{5}{32}, \frac{5}{32}, \frac{1}{8}, \frac{3}{32}, \frac{1}{16}, \frac{1}{32}\right]$ | 1 |
| 1024 | $\left[\frac{3}{64}, \frac{3}{64}, \frac{1}{16}, \frac{1}{16}, \frac{5}{64}, \frac{5}{64}, \frac{5}{64}, \frac{5}{64}, \frac{5}{64}, \frac{1}{16}, \frac{1}{16}, \frac{3}{64}, \frac{3}{64}\right]$ | 1 |

The resulting waveform is then fed into a FIR filter which implements a moving average. Its length N depends on the sampling frequency and may be determined, for example, according to Table 6

TABLE 6

Moving Average Filter Length

| Fs [Hz] | MA Filter Length [samples] |
|---|---|
| 128 | 16 |
| 256 | 32 |
| 512 | 64 |
| 1024 | 128 | and it is implemented with the following equation:

$$y_n = \frac{1}{N}[x_n + \ldots + x_{n-N+1}] \quad (6)$$

The output of this long filtering chain is a feature signal representing the QRS complex energy in the signal, similar to a bump-like waveform. Each bump corresponds to the occurrence of a QRS complex, therefore by detecting the peaks in this signal we may identify the presence of every heart beat. The peak detection algorithm and the subsequent QRS detection logic are executed as disclosed in the prior article by Hamilton and Tompkins [3].

Branch #2: Morphological Features Estimation

The second branch of the system is configured to estimate several important morphological features about the detected QRS complex. Bandpass filtering techniques may drop most of the noise affecting the ECG, but in doing so the morphology of the QRS complex is often altered and it loses most of its physiological information. That's the reason for the presence of a second branch, where filtering is very low and it is limited to the removal of baseline wanders, power-line interference and high-frequency noise. The first two filters are the same of the first branch, while the distinctive features of this branch are the lowpass filter 16 (FIG. 2) and the morphological features extraction block 18.

Lowpass Filter

The filter 16 is configured to drop high frequency noise without altering the ECG signal in the band of P and T waves and the QRS complex (0-40 Hz). This filter is preferably a FIR low-pass filter, whose length and coefficients change according to the choice of the sampling frequency.

This low-pass filter is optional and may be omitted at the cost of worsening performances of the morphological features extraction. Simulations showed that when the working (sampling) frequency is about 250 Hz or smaller, this filter may be omitted still obtaining a reliable morphological features extraction.

Morphological Features Extraction

Several important morphological features may be extracted from the QRS complex. All of them are extremely important in identifying the nature of the heart beat and in distinguishing a normal beat from an arrhythmia. The block 18 is capable of estimating the following features:

QRS complex width
R wave peak height
P wave height
PR interval length

This block process two different signals: the first is the output of the first two blocks of Branch #2, the second is the sloped version of the first one (see the R wave peak detection block in Branch #1 for information about the slope filter). Moreover an enable signal is present, coming from the R wave peak detection block. Every time a QRS is detected by the R wave peak detector 20, the morphological features extraction block 18 is activated. The detection of the R wave peak is the starting point for the subsequent estimations and is important as far as the heart rate estimation is concerned. The R wave peak is detected as the zero crossing between the two absolute maximums of the sloped version of the filtered signal. The assumption behind this choice is that the R wave peak is usually the turning point between the two steepest parts of the QRS complex. After identifying the R wave peak, its index is used as a starting base for the estimation of the QRS complex width. In order to identify the peaks of the Q and S waves, two different strategies are implemented. The first one is based on the filtered signal and detects when it returns to the baseline on the left and on the right of the R wave peak. The second one is based on the sloped signal and detect when it falls below a certain threshold, which is estimated as a fraction of the maximum absolute value of the slope in the signal. The P wave peak is detected as the highest peak in the signal in a window starting 250 ms before the R wave peak and ending 50 ms before the same peak. Finally the estimation of the PR interval length is straightforward, being it the difference between the index of the R wave peak and the index of the P wave peak.

Branch #1+#2: Beat Validation and Classification

The outputs from the first two branches are then received by the beat validation and classification module 22. It is configured to classify the detected beats and establish the typical waveform for a normal beat of the patient. Preferably, it is capable of detecting and classifying several basic type of arrhythmias:

premature ventricular contraction;

premature atrial contraction;

ventricular tachycardia;

supraventricular tachycardia.

The block uses the template memory 24 (FIG. 2) to store all information about the ECG waveform of the patient. It contains the samples of the specific patient ECG waveform and the measures of the morphological parameters of interest. This structure is initialized by a typical QRS pattern and in the start-up phase, the first beat encountered is compared with this pattern. Similarity between the two sequences is estimated by synchronizing them according to the R wave peak and by computing the correlation coefficient. If the correlation value exceeds a fixed threshold, the first beat is classified as normal, its waveform is stored in the template memory 24 and it is then used for the following comparisons. Whenever a normal beat is detected, the reference waveform is updated with the new beat (an average is computed between the reference template and the new beat). If the correlation is lower than the fixed threshold but above a second fixed threshold, the beat is classified as "uncertain" (it may be or a PVC or a noisy normal beat). If the correlation is lower than the second fixed threshold, it is classified as noise. The morphological features of the beat are stored as well, and they will be used in assessing the nature of the beat. After a fixed number of normal beats has been correctly identified, the mean RR interval (distance between a R wave peak and the previous one) is computed and used to estimate the prematurity of the analyzed beat. If a beat is premature and has a high correlation is a PAC. If a beat is premature and has a lower correlation, it is a PVC. The output of this block is the classification of the detected beat. This information is fed into the heart rate estimation block 40 to compute the heart rate of the patient.

Branch #3: High Frequency Noise Detection

This branch is designed to estimate the high frequency components in the signal and eventually issue a warning about the low quality of the ECG. A clean ECG is generally characterized by a power spectrum where most of the energy is included between 0 and 35 Hz. P and T waves have spectral components between the DC and 10 Hz, while the QRS complex energy is usually between 10 and 35 Hz. Thus spectral components which exceed 40 Hz does not concern the typical electrical activity of the heart and may be definitely considered a noise source for the algorithm (e.g., electromyographic activity, bad electrode contact).

High-Pass Filter

The raw signal is filtered using a high-pass FIR filter 32 with a cut-off frequency of 45 Hz. As usual, the number of taps and the coefficients depends on the choice of the sampling frequency and may be determined, for example, according to Table 7.

TABLE 7

| High-Frequency Noise Filter | | |
|---|---|---|
| Fs [Hz] | h(n) | gain |
| 128 | $\left[\frac{5}{32}, -\frac{3}{16}, \frac{7}{32}, -\frac{3}{16}, \frac{5}{32}\right]$ | 1 |
| 256 | $\left[\frac{1}{8}, 0, -\frac{1}{8}, -\frac{1}{4}, \frac{5}{8}, -\frac{1}{4}, -\frac{1}{8}, 0, \frac{1}{8}\right]$ | 1 |

TABLE 7-continued

| High-Frequency Noise Filter | | |
|---|---|---|
| Fs [Hz] | h(n) | gain |
| 512 | $\left[\begin{array}{c} 0, 0, 0, \frac{1}{16}, \frac{1}{16}, 0, 0, -\frac{1}{16}, -\frac{1}{16}, -\frac{1}{32} \\ -\frac{1}{32}, -\frac{3}{16}, \frac{13}{16}, -\frac{3}{16}, -\frac{1}{32}, -\frac{1}{32}, -\frac{1}{16}, \\ -\frac{1}{16}, 0, 0, \frac{1}{16}, \frac{1}{16}, 0, 0, 0 \end{array}\right]$ | 1 |
| 1024 | $\left[\begin{array}{c} 0, 0, 0, 0, 0, 0, 0, 0, 0, -\frac{1}{16}, -\frac{1}{16}, -\frac{1}{16}, \\ -\frac{1}{8}, -\frac{1}{8}, -\frac{1}{8}, \frac{14}{16}, -\frac{1}{8}, -\frac{1}{8}, -\frac{1}{8}, \\ -\frac{1}{16}, -\frac{1}{16}, -\frac{1}{16}, 0, 0, 0, 0, 0, 0, 0, 0 \end{array}\right]$ | 1 |

High Frequency Noise Detection System

Figure 8:
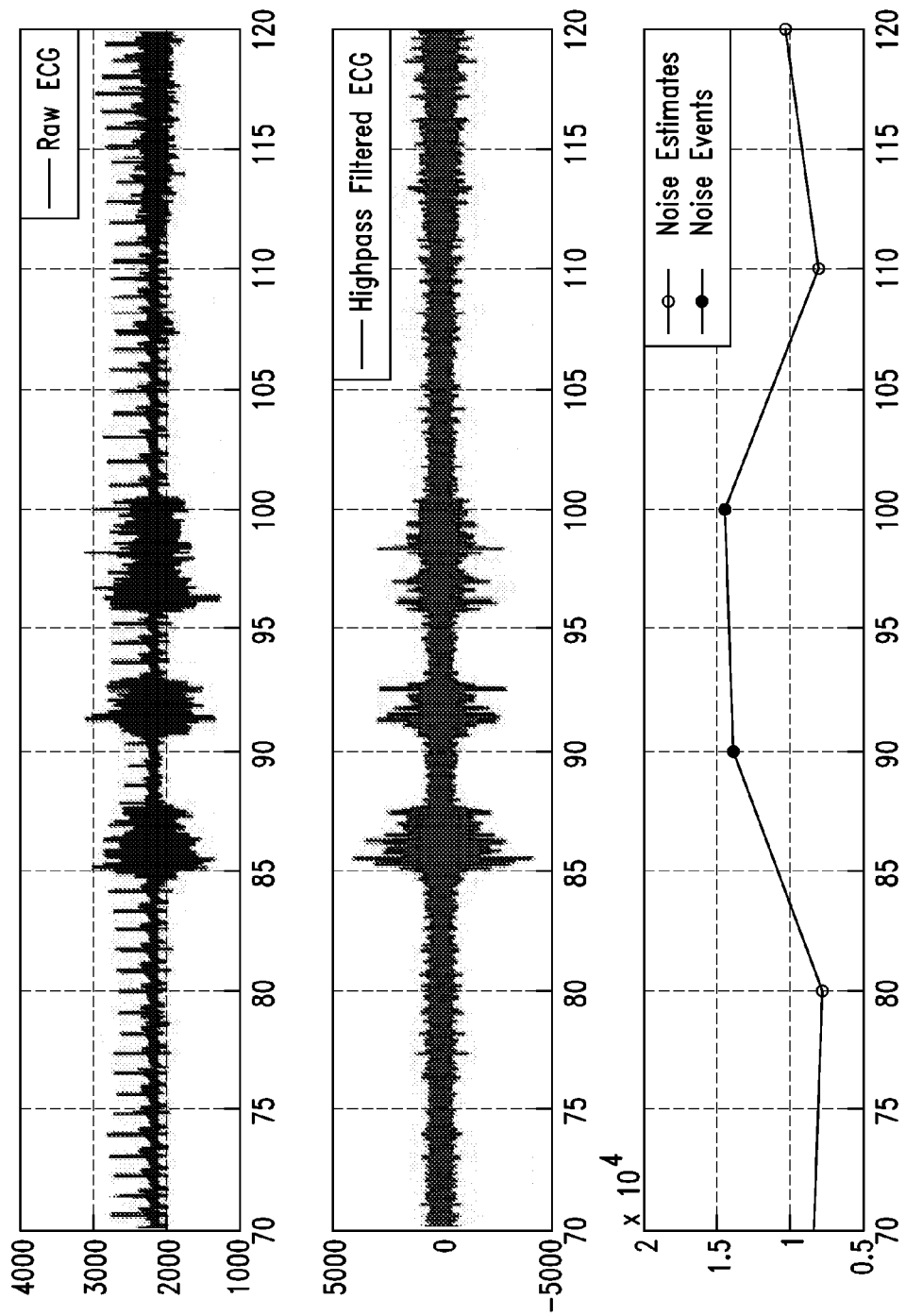
FIG. 8 depicts exemplary waveforms for illustrating a way of detecting high frequency noise superposed to the processed ECG signal.

The filtered signal is then processed by a block 34 which estimates the level of high frequency noise. This is accomplished by computing the integral (area under the curve) of the filtered signal every 2 seconds. Five consecutive estimates are averaged in a 10-second interval, providing an estimate of the high frequency noise level of the interval. After a start-up phase, where 4 intervals are acquired and analyzed, a threshold is computed as a percentage of the mean high frequency noise level, and every following interval with noise exceeding that threshold is marked as unreliable, returning a warning in the output (FIG. 8).

Branch #4: Disconnection Detection

The electrode detector 36 is responsible of detecting any disconnection during the acquisition of the ECG. Whenever the electrodes lose contact from the chest of the patient, the signal exhibits a peculiar behavior, saturating to the top or the bottom of the range. After a few seconds, the signal is completely affected by the power-line interference and thus presents fast oscillations above and under the DC.

Electrodes Disconnection Detection

Figure 9:
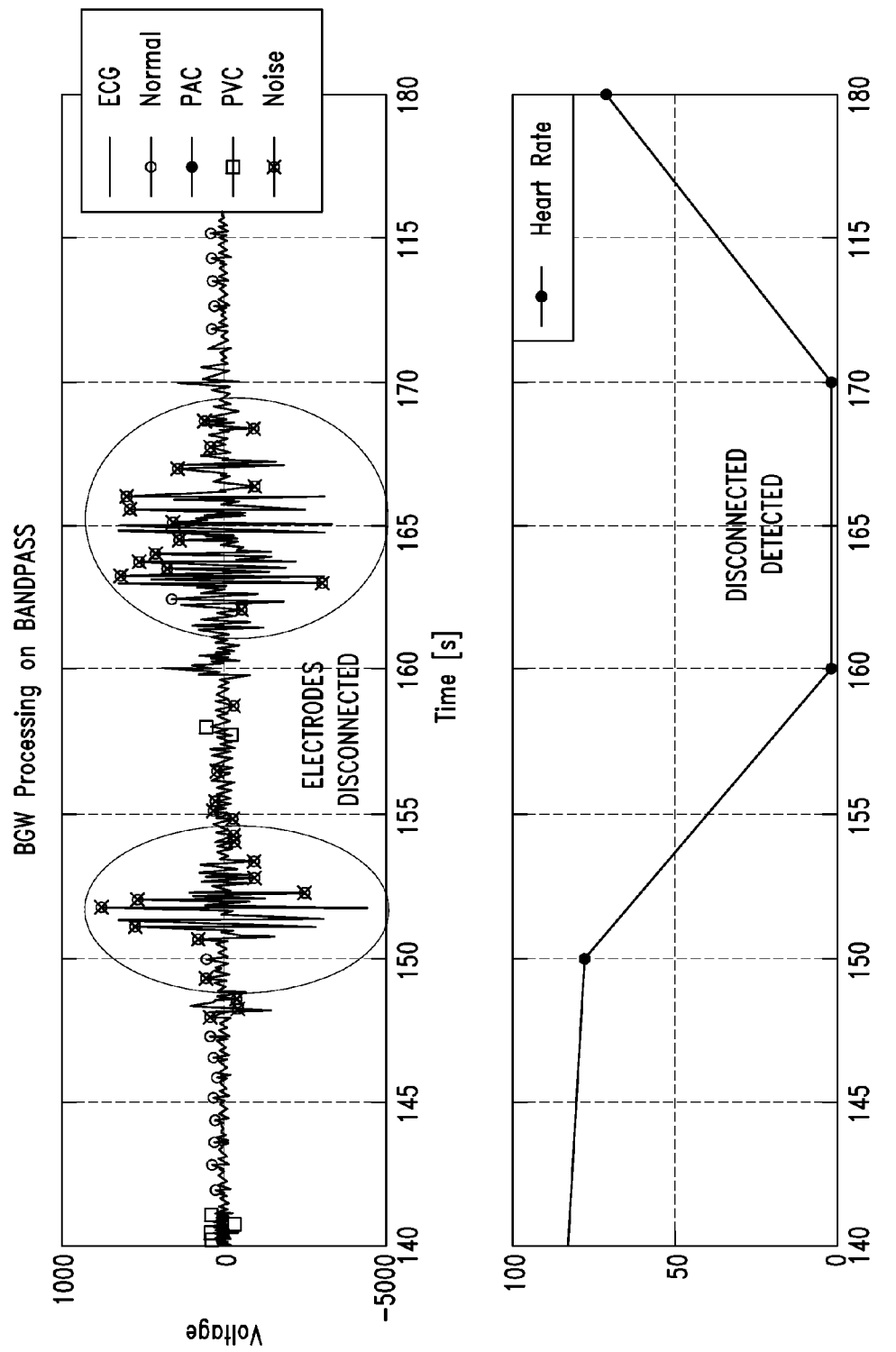
FIG. 9 depicts exemplary waveforms for illustrating a way of detecting disconnection of electrodes.

In order to detect a disconnection event, every 10-second interval of the ECG signal is checked and if the number of samples near the top or the bottom of the signal range (i.e., saturation) exceeds a specific threshold, a disconnection error is produced as output (FIG. 9).

Power-Line Interference Detection

Power-line interference may be effectively detected in the powerline interference detector 38 by counting the number of zero crossings affecting the ECG signal. For a clean ECG signal, the number of zero crossings is extremely lower than the number of zero crossings during a disconnection. Therefore if the zero crossings counted exceeds a specific threshold, a disconnection warning is issued.

All Branches Combined: Heart Rate Estimation

The heart rate estimator 40 is the final block of the system and is responsible of computing the reliable heart rate estimation, using the output of the four branches to improve the quality of the estimation. This block operates over a 10-second window and returns a heart rate estimation based on the average of the beats detected in these 10 seconds. The first two branches provide the estimation of the RR interval and the classification of the heart beat detected. Only consecutive normal beats are used to estimate the heart rate. The third and the fourth branches check the quality of the signal and, if needed, return a warning output that marks the heart rate estimation as unreliable. The mean RR interval is computed as:

$$RR_{MEAN} = \frac{RR_n + \ldots + RR_{n-N+1}}{N} \quad (3)$$

The corresponding heart rate, measured in beat-per-minutes (bpm), is calculated with the formula:

$$HR_n = \frac{60}{RR_{MEAN}} \quad (4)$$

The block 40 returns the computed heart rate only if both branches #3 and #4 does not return a warning about the quality of the signal (high frequency noise or disconnection). If instead the signal quality is not satisfying, the heart rate holds to the last reliable value and the system issues a visual or audio warning to the user, suggesting an electrode check.

Figure 10:
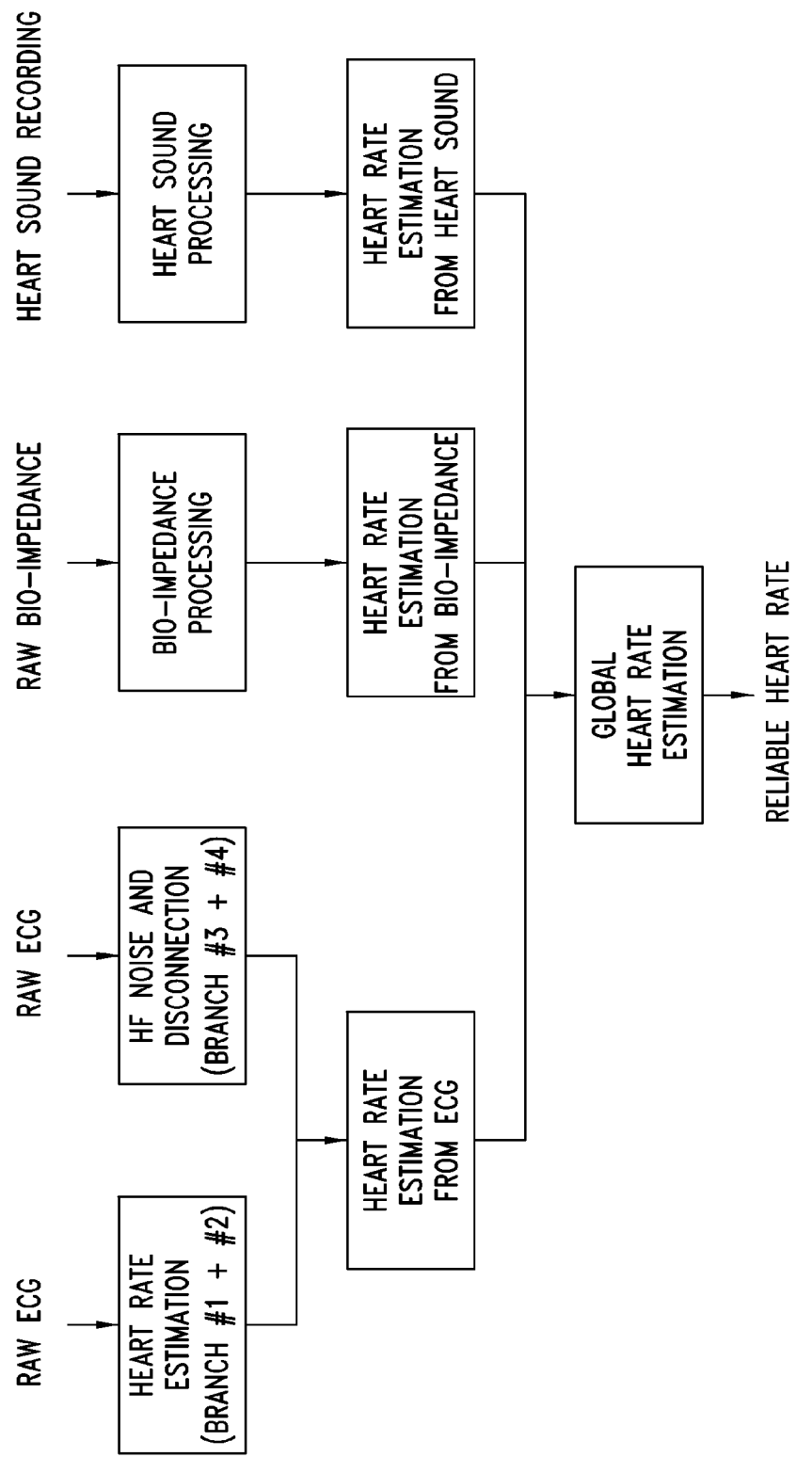
FIG. 10 illustrates how to obtain more accurate heart rate estimation by combining the results of the novel method with the results obtained through bio impedance measurements and heart sound recording.

It must be noted that the third through fifth branches are not actually necessary to perform a reliable heart rate estimation. Branches 3-5 improve the performance of the processing chain, but are not mandatory. The method may be expanded with the heart rate estimation from other physiological sources as well, leading to a even more reliable estimate, as illustrated in FIG. 10.

Implementation and Testing

The algorithm of FIG. 5 has been preliminary implemented with the MATLAB programming language, then it has been successfully ported and implemented in C and tested on a STM32 high performance low power microcontroller. The STM32 microcontroller incorporates a high-performance ARM Cortex-M3 32-bit RISC core operating at 72 MHz frequency, high-speed embedded memories, and an extensive range of enhanced I/Os and peripherals connected to two APB buses.

REFERENCES

[1] B. U. Kohler, C. Henning, and R. Orglmeister, "The principles of software QRS detection," *IEEE Engineering in Medicine and Biology Magazine,* 1(21):42-57, January-February 2002.
[2] J. Pan, W. J. Tompkins, "A Real-Time QRS Detection Algorithm", IEEE Trans. Biomed. Eng., vol. BME-32, no. 3, pp. 230-236, 1985.
[3] P. S. Hamilton and W. J. Tompkins, "Quantitative Investigation of QRS Detection Rules Using the MIT/BIH Arrhythmia Database," *IEEE Transactions on Biomedical Engineering,* 12(33):1157-65, December 1986.
[4] P. Hamilton, "Open Source ECG Analysis", Computers in Cardiology, vol. 29, pp. 101-104, 2002
[5] Documentation of the Open Source ECG Analysis software, release No 1.21, downloadable from http://www.eplimited.com/osea13.pdf
[6] Marco Pessione, "Low-Complexity Adaptive Reliable Electrocardiogram Feature Extraction", Master's thesis discussed on Jan. 27, 2009, Politecnico di Torino.

The various embodiments described above can be combined to provide further embodiments. All of the U.S. patents, U.S. patent application publications, U.S. patent applications, foreign patents, foreign patent applications and non-patent publications referred to in this specification are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method, comprising:
    filtering a digital replica of an electrocardiogram (ECG) signal with a passband filter with cut-off frequencies of about 10 Hz and 35 Hz, the filtering the digital replica including generating a corresponding passband signal;
    filtering out a direct current component from said digital replica of the ECG signal, the filtering out the direct current component including generating a corresponding alternating current (AC) signal; and
    detecting occurrence of peaks of R waves of the ECG signal by:
        processing the passband signal with a finite impulse response filter having a pulse response that is linearly increasing, the processing including generating an intermediate signal; and
    detecting peaks of R waves at zero-crossings between two consecutive maxima of said intermediate signal.

2. The method of claim 1, further comprising:
    in response to detecting peaks of R waves of the ECG signal, generating estimations of a morphological feature of heart beats represented in the ECG signal by processing the AC signal, the morphological feature being one of a set consisting of width of QRS complex, height of peaks of R or P waves, and lengths of PR intervals.

3. The method of claim 2, wherein said estimations are generated by processing a replica of said AC signal blanked for an interval of about 50 ms after the occurrence of an R wave peak, according to the Hamilton-Tompkins algorithm.

4. The method of claim 1, wherein filtering out the direct current component from said ECG signal is performed before filtering the AC signal with the passband filter with cut-off frequencies of about 10 Hz and 35 Hz.

5. The method of claim 1, further comprising detecting disconnection from a patient of an electrode configured to detect the ECG signal, the detecting occurrence of peaks including determining that a number of samples of the ECG signal are above or below a useful signal range.

6. A non-transitory computer readable memory medium storing processor instructions configured to cause a processor to execute a method comprising:
    filtering an electrocardiogram (ECG) signal with a passband filter with cut-off frequencies of about 10 Hz and 35 Hz, the filtering the ECG signal including generating a corresponding passband signal;
    filtering out a direct current component from said ECG signal, the filtering out the direct current component including generating a corresponding alternating current (AC) signal;
    detecting occurrence of peaks of R waves of the ECG signal by processing the passband signal; and
    in response to detecting peaks of R waves of the ECG signal, generating estimations of a morphological feature of heart beats represented in the ECG signal by processing a replica of said AC signal blanked for an interval of about 50 ms after the occurrence of an R wave peak, according to the Hamilton-Tompkins algorithm, the morphological feature being one of a set consisting of width of QRS complex, height of peaks of R or P waves, and lengths of PR intervals.

7. The non-transitory computer readable memory medium of claim 6, wherein the filtering steps are performed on a digital replica of the ECG signal, and said peaks of R waves of the ECG signal are detected by:
- processing said passband signal with a slope filter, generating an intermediate signal; and
- detecting peaks of R waves at zero-crossings between two consecutive maxima of said intermediate signal.

8. The non-transitory computer readable memory medium of claim 6, wherein the method further comprises detecting disconnection from a patient of an electrode configured to detect the ECG signal, the detecting disconnection including determining that a number of samples of the ECG signal are above or below a useful signal range.

9. An ECG signal monitor, comprising:
- a passband filter, with cut-off frequencies of about 10 Hz and 35 Hz, configured to filter an electrocardiogram (ECG) signal and generate a corresponding passband signal;
- a DC filter configured to filter out a direct current component from said ECG signal and generate a corresponding alternating current (AC) signal;
- a peak detector configured to detect occurrence of peaks of R waves of the ECG signal by processing the passband signal; and
- a morphological feature extractor configured to, in response to the peak detector detecting peaks of R waves of the ECG signal, generate estimations of a morphological feature of heart beats represented in the ECG by processing a replica of said AC signal blanked for an interval of about 50 ms after the occurrence of an R wave peak, according to the Hamilton-Tompkins algorithm, the morphological feature being one of a set consisting of width of QRS complex, height of peaks of R or P waves, and lengths of PR intervals.

10. The monitor of claim 9, wherein the peak detector includes:
- a slope filter configured to detect slope of the passband signal and generate an intermediate signal; and
- a moving average filter configured to process said intermediate signal and generate a moving average of a number of samples of the intermediate signal.

11. The monitor of claim 9, further comprising:
- a plurality of electrodes configured to detect an analog ECG signal of a patient;
- an analog circuit configured to process the analog ECG signal; and
- an analog/digital converter configured to convert the analog ECG signal to a digital ECG signal, wherein the DC filter is configured to process the digital ECG signal.

12. The monitor of claim 11, further comprising:
- an electrode disconnect detector configured to detect disconnection of one or more of the electrodes from the patient by determining that a number of samples of the digital ECG signal are above or below a useful signal range.

* * * * *